United States Patent
Glaug et al.

(10) Patent No.: US 8,198,504 B2
(45) Date of Patent: Jun. 12, 2012

(54) THERMAL SIGNAL TAMPON PLEDGET

(75) Inventors: Frank S. Glaug, Chester Springs, PA (US); Keith J. Edgett, Middletown, DE (US)

(73) Assignee: Playtex Products, LLC, Shelton, CT (US)

( * ) Notice: Subject to any disclaimer, the term of this patent is extended or adjusted under 35 U.S.C. 154(b) by 0 days.

(21) Appl. No.: 12/042,562

(22) Filed: Mar. 5, 2008

(65) Prior Publication Data

US 2009/0227974 A1   Sep. 10, 2009

(51) Int. Cl.
*A61F 13/15* (2006.01)
*A61F 13/20* (2006.01)

(52) U.S. Cl. .......................................... 604/361

(58) Field of Classification Search .................. 604/345, 604/361
See application file for complete search history.

(56) References Cited

U.S. PATENT DOCUMENTS

| | | | | |
|---|---|---|---|---|
| 3,794,024 A | * | 2/1974 | Kokx et al. | 604/361 |
| 4,317,454 A | * | 3/1982 | Bucalo | 600/572 |
| 5,681,298 A | * | 10/1997 | Brunner et al. | 604/361 |
| 5,702,376 A | * | 12/1997 | Glaug et al. | 604/361 |
| 5,728,125 A | * | 3/1998 | Salinas | 604/361 |
| 5,769,813 A | * | 6/1998 | Peiler et al. | 604/11 |
| 6,596,919 B2 | * | 7/2003 | Williams | 604/361 |
| 7,338,516 B2 | * | 3/2008 | Quincy et al. | 607/96 |
| 2002/0107494 A1 | * | 8/2002 | Williams | 604/361 |

FOREIGN PATENT DOCUMENTS

| | | |
|---|---|---|
| GB | 1433415 | 4/1976 |
| KR | 10-0194528 | 6/1999 |
| WO | 02/058587 A2 | 8/2002 |

OTHER PUBLICATIONS

Notice of Preliminary Rejection with English Translation, Mailing Date—Jan. 11, 2012, issued in conjunction with KR Patent Application No. 10-2010-7022184.

Examination Report, Mailing Date—Dec. 13, 2011, issued in conjunction with GB Patent Application No. GB1014520.9.

* cited by examiner

*Primary Examiner* — Tatyana Zalukaeva
*Assistant Examiner* — Ginger T Chapman
(74) *Attorney, Agent, or Firm* — Michaud-Kinney Group LLP

(57) ABSTRACT

In a tampon pledget, a quantity of moisture activated material is positioned in contact with, or adjacent to a layer of absorbent material used in forming the pledget. Upon contact with menses, the moisture activated material reacts in one of an endothermic and exothermic manner so that in use, the pledget, when forming part of a tampon can thermally alert a wearer when the pledget has reached its absorbent capacity.

20 Claims, 1 Drawing Sheet

THERMAL SIGNAL TAMPON PLEDGET

FIELD OF THE INVENTION

The present invention relates generally to tampon pledgets and more particularly to tampon pledgets that provide an indication to a user that a tampon in which the pledget is incorporated, is ready to be changed.

BACKGROUND

Due to the impracticality associated with removing a tampon to ascertain whether or not it has reached its absorbent limit, it is typically difficult to determine the appropriate time for replacement. Currently there are no indicators that are built into a tampon to signal the consumer that the tampon is close to full capacity. The consumer, therefore, is left with having to rely on instinct when making the determination as to when to change the tampon. This can often result in the tampon being changed prior to reaching full saturation, or subsequent to reaching full saturation when the tampon is changed too late, thereby increasing the potential for leakage past the tampon.

Based on the foregoing, it is the general object of the present invention to provide a tampon that employs some indication that allows a user to discretely determine when tampon change is necessary.

SUMMARY OF THE INVENTION

The present invention resides in one aspect in a tampon pledget having at least two layers of absorbent material that are formed into the pledget. A quantity of moisture activated material is positioned in contact with and/or adjacent to one of the layers of absorbent material. Upon contact with menses, the moisture activated material reacts in one of an exothermic and an endothermic manner so that during use, the pledget, when forming part of a tampon, can alert a user when the absorbent capacity of the tampon has been reached.

Preferably, where the reaction is endothermic, the above-described moisture activated material is made from at least one of salt hydrates, anhydrous salts and organic compounds. Where a salt hydrate is employed, it is preferable that the moisture activated material be at least one of sodium acetate, sodium carbonate, sodium sulfate, sodium thiosulfate, or sodium phosphate. Where anhydrous salts are used, it is preferable that the moisture activated material be at least one of ammonium nitrate, potassium nitrate, ammonium chloride, potassium chloride and sodium nitrate. When the moisture activated material is organic, the preferred materials include one or more of urea and xylitol.

In an embodiment of the present invention, the moisture activated material is positioned in a packet with the packet being located between layers of material that are ultimately formed into the pledget so that upon formation of the pledget, the packet is located interior of an outer surface defined by the pledget. The packet can be formed from at least two layers of nonwoven material bonded together with the moisture activated material positioned therebetween. The nonwoven material can be bonded together by using one or more of adhesives, heat sealing, stitching, and ultrasonic bonding. The packet can also be formed from a single piece of nonwoven material folded over onto itself with the edges of the folded nonwoven material being bonded together in the above-described manner. Preferably, the moisture activated material is in particulate or powder form; however, the present invention is not limited in this regard as the moisture activated material can also be in sheet form without departing from the broader aspects of the present invention.

In another embodiment of the present invention, rather than being positioned in the above-described packet, the moisture activated material is dispersed within, and on a surface of a first of the at least two layers of absorbent material. A second of the at least two layers of absorbent material is positioned over the surface of the first layer of absorbent material so that upon formation of the layers of absorbent material into the pledget, the moisture activated material is located interior of an outer surface defined by the pledget. Accordingly, where the pledget forms part of a tampon, once moisture absorbed by the pledget reaches the moisture activated material, an endothermic or exothermic reaction occurs which is discretely detectable by a user and provides an indication regarding the need to change the tampon.

DETAILED DESCRIPTION OF THE PREFERRED EMBODIMENTS

The tampon pledget of the present invention comprises a moisture activated material that produces either an endothermic or exothermic reaction upon contact with moisture. The moisture activated material reacts to (is "activated by") contact with menstrual fluid by absorbing heat from, or releasing heat to, the surrounding area. The moisture activated material is located interior of an outer surface of the pledget. Accordingly, once activated, the moisture activated material causes a temperature change within the pledget that is detectable by a wearer of the tampon. A tampon typically includes a removal string at the distal end of the tampon. Preferably, the moisture activated material is disposed at or near the string end of the tampon, so that it will be activated when the tampon is near full saturation due to contact with bodily fluid. Preferably, there is substantially no moisture activated material at the insertion end (i.e., the proximal end) of the tampon.

In use, the above-described tampon including the pledget having the moisture activated material forming a part thereof is inserted in the body. When the moisture activated material in the tampon comes into contact with menses, the user senses the temperature change and is thereby signaled that the tampon is ready to be replaced.

The moisture activated material may be a heat-absorbing material that produces an endothermic reaction, such as sodium acetate, sodium carbonate, sulfate, thiosulfate, phosphate or anhydrous salts such as ammonium nitrate, potassium nitrate, ammonium chloride, potassium chloride, and sodium nitrate, or organic compounds such as urea or a sugar such as xylitol.

Alternatively, the temperature-change material may be a heat-releasing material that produces an exothermic reaction such as aluminum chloride, aluminum sulfate, potassium aluminum sulfate or the like.

Figure 1:
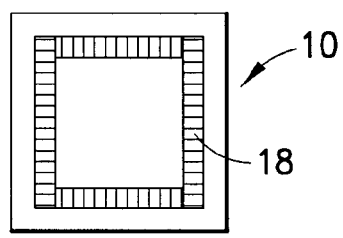
FIG. 1 is a schematic plan view of a temperature-change packet for use in one embodiment of the present invention.
Figure 2:
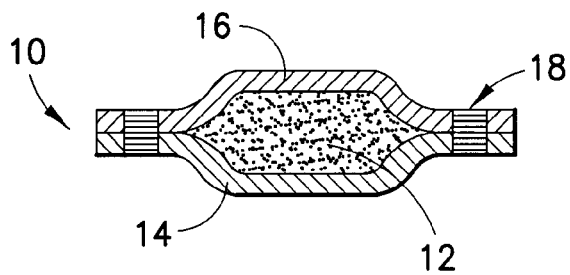
FIG. 2 is a cross-sectional view of the temperature-change packet of FIG. 1.

The moisture activated material may be in particulate or powder form and may be packaged in between layers of a permeable, non-woven material to provide a temperature-change packet as shown in FIG. 1 and FIG. 2. The temperature-change packet 10 includes the moisture activated material 12 that is disposed in between layers 14 and 16 of the permeable, non-woven material. The layers 14, 16 may be sealed together by an adhesive, heat seal, ultrasonic bond, stitching, or any other suitable means or any combination of the foregoing, to form a perimeter seal 18 around the moisture activated material. The layers 14 and 16 of the permeable, non-woven material may comprise spunbond polypropylene (SBPP), spunbond-meltblown-spunbond (SMS), thermally bonded webs, chemically bonded webs, through-air-bonded carded webs (TABCW), carded-and-needle-punched webs, hydro-entangled webs, cotton/polypropylene webs, PET (polyester) webs, spunlace, airlaids, meltblowns, apertured films, tissues, etc. Preferably, the permeable, non-woven material is suitable for high temperature processing (e.g., handling at temperatures of about 300° F. or higher). In a particular embodiment, the layers 14 and 16 are made from a composite comprising about 30% cotton and about 70% polypropylene fibers, by weight, and has a basis weight of 33 gsm (grams per square meter). A non-woven material found to be useful in making the packets is SH-PPC-33 manufactured by Shalag Nonwoven of Israel. Optionally, the layer 16 may be a folded-over portion of the layer 14.

Figure 3:
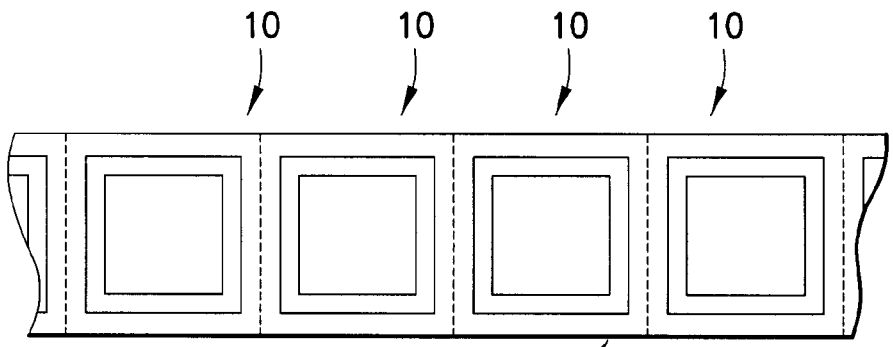
FIG. 3 is a schematic plan view of a continuous length of temperature-change packets.

Optionally, the layers 14 and 16 may comprise lengths of material with which a plurality of packets are formed to provide a length 20 of interconnected temperature-change packets 10 as shown in FIG. 3. The length 20 of temperature-change packets may be wound up in pancake rolls or traverse spools. A length 20 of temperature-change packets 10 may then be installed on a tampon manufacturing machine. The length 20 of temperature-change packets 10 may be unwound and cut into individual temperature-change packets 10 for incorporation into temperature-change pledgets.

Figure 4:
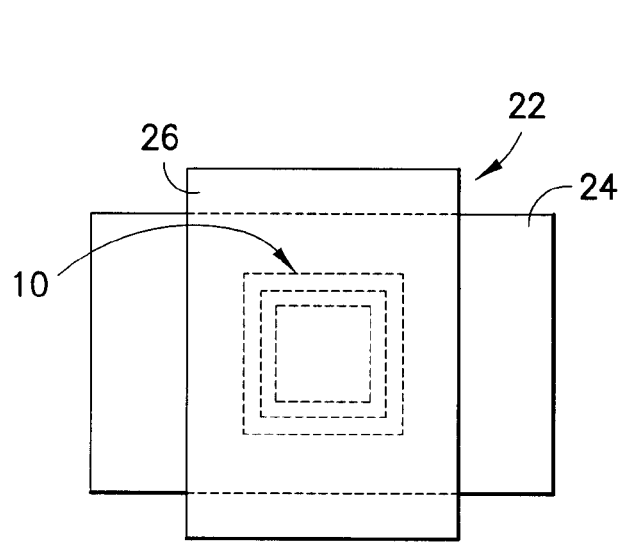
FIG. 4 is a schematic plan view of the temperature-change packet of FIG. 1 in place between layers of a tampon pledget.

As shown in FIG. 4, a pledget 22 is formed by placing an individual temperature-change packet 10 on a first layer 24 of pledget material. A second layer 26 of pledget material is then placed on the first layer 24. The pledget 22 is used to form a tampon with the temperature-change packet 10 therein near the string end of the tampon.

In another embodiment of the present invention, a moisture activated material is dispensed on top of, and in the central area of, a first layer 24 of pledget material. A second layer 26 of pledget material is placed over the moisture activated material to sandwich the moisture activated material 12 between the layers 24 and 26 of pledget material. The layers 24, 26 of pledget material are used to form a temperature-change pledget that is used to form the tampon. Preferably, the moisture activated material is disposed near the string end of the tampon.

In another embodiment, moisture activated material 12 is blended into the binder (polymer) and the absorbent (cellulose, cotton and/or rayon) fibers that form pledget material. For example, particles of moisture activated material 12 are blended into an airlaid web that is used to make layered pledget composites. The moisture activated material-containing airlaid web is incorporated into the pledget material so as to be concentrated near the string end of the tampon.

Figure 5:
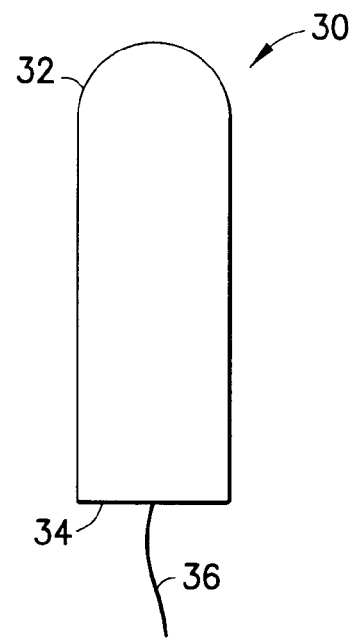
FIG. 5 is a cross-sectional view of a tampon as described herein.

A tampon 30 is shown in FIG. 5. The tampon 30 has a proximal end 32, a distal end 34 and a removal string 36 attached at the distal end 34. The tampon 30 comprises a moisture activated material as described herein, principally at the distal end 34. There is substantially no moisture activated material at or near the proximal end 32.

The terms "first," "second," and the like herein do not denote any order, quantity, or importance, but rather are used to distinguish one element from another. In addition, the terms "a" and "an" herein do not denote a limitation of quantity, but rather denote the presence of at least one of the referenced item.

Although the invention has been described with reference to particular embodiments thereof, it will be understood by one of ordinary skill in the art, upon a reading and understanding of the foregoing disclosure, that numerous variations and alterations to the disclosed embodiments will fall within the spirit and scope of this invention and of the appended claims.

What is claimed is:

1. A tampon pledget, comprising:
   an outer surface;
   at least two layers of absorbent material formed into said pledget;
   a quantity of moisture activated material positioned between said at least two layers of absorbent material such that said moisture activated material is located interior to said outer surface of said tampon pledget; and wherein
   upon contact with menses said moisture activated material reacts in one of an exothermic and an endothermic manner so that in use, said pledget thermally alerts a user when said pledget has reached its absorbent capacity.

2. A tampon pledget as defined by claim 1 wherein said moisture activated material is endothermic and is made from at least one of salt hydrates, anhydrous salts and organic compounds.

3. A tampon pledget as defined by claim 2 wherein said moisture activated material is a salt hydrate comprising at least one of sodium acetate, sodium carbonate, sodium sulfate, sodium thiosulfate, and sodium phosphate.

4. A tampon pledget as defined by claim 2 wherein said moisture activated material is an anhydrous salt comprising at least one of ammonium nitrate, potassium nitrate, ammonium chloride, potassium chloride and sodium nitrate.

5. A tampon pledget as defined by claim 2 wherein said moisture activated material is an organic compound comprising at least one of urea and xylitol.

6. A tampon pledget as defined by claim 1 wherein:
   said quantity of moisture activated material is positioned within a packet; and
   said packet is positioned between said at least two layers of absorbent material.

7. A tampon pledget as defined by claim 6 wherein said packet is formed from at least two layers of nonwoven material bonded together with said moisture activated material positioned therebetween.

8. A tampon pledget as defined by claim 7 wherein said at least two layers of nonwoven material are bonded together by at least one of adhesives, heat sealing, ultrasonic bonding, and stitching.

9. A tampon pledget as defined by claim 7 wherein said packet is formed from a single piece of nonwoven material that is folded onto itself to form said at least two layers of nonwoven material, and wherein edges defined by said folded piece of nonwoven material are bonded together to form said packet.

10. A tampon pledget as defined by claim 9 wherein said edges are bonded together by at least one of adhesives, heat sealing, ultrasonic bonding, and stitching.

11. A tampon pledget as defined by claim 7 wherein said nonwoven material comprises at least one of spunbound polypropylene, spunbound-meltblown-spunbound, thermally bonded webs, chemically bonded webs, through-air bonded carded webs, carded and needle punched webs, hydro-entangled webs, cotton/polypropylene webs, spunlace, airlaids, meltblowns, aperture films, and tissues.

12. A tampon pledget as defined by claim 7 wherein said nonwoven material can withstand high temperature processing at between about 300° F. to about 400° F.

13. A tampon pledget as defined by claim 7 wherein said nonwoven material is a composite comprising about 30% cotton and about 70% polypropylene fibers, by weight.

14. A tampon pledget as defined by claim 13, wherein said nonwoven material has a basis weight of about 33 gsm.

15. A tampon pledget as defined by claim 7 wherein said moisture activated material is in particulate form dispersed between said at least two layers of nonwoven material.

16. A tampon pledget as defined by claim 7 wherein said moisture activated material is in powder form.

17. A tampon pledget as defined by claim 1 wherein said moisture activated material is dispersed within, and on a surface of a first of said at least two layers of absorbent material and a second of said at least two layers of absorbent material is positioned over said surface of said first layer of absorbent material.

18. A tampon pledget as defined by claim 1 wherein, upon formation of said at least two layers of absorbent material into said pledget, said moisture activated material is concentrated adjacent a distal end of said pledget.

19. A tampon pledget comprising:
   at least two layers of absorbent material; and
   a quantity of moisture activated material blended into at least one layer of absorbent material, wherein said moisture activated material is located interior of an outer surface of said tampon pledget, so that upon contact with menses, said moisture activated material reacts in one of an endothermic and exothermic manner, thermally alerting a user when said pledget has reached its absorbent capacity.

20. A tampon pledget as defined by claim 19, wherein said quantity of moisture activated material is located adjacent a distal end of said pledget.

* * * * *